United States Patent [19]

Popovich

[11] Patent Number: 5,628,073
[45] Date of Patent: May 13, 1997

[54] SAUNA

[75] Inventor: John Popovich, Del Mar, Calif.

[73] Assignee: Watkins Manufacturing Corp., Vista, Calif.

[21] Appl. No.: 508,041

[22] Filed: Jul. 27, 1995

[51] Int. Cl.$^6$ ............................................. A61H 33/06
[52] U.S. Cl. ....................... 4/524; 4/528; 135/115; 135/124
[58] Field of Search .................... 4/524, 526, 527, 4/528, 531; 135/98, 99, 115, 124, 900, 901

[56] References Cited

U.S. PATENT DOCUMENTS

| | | |
|---|---|---|
| D. 240,667 | 7/1976 | Hall . |
| 1,979,094 | 10/1934 | Blunt . |
| 2,948,287 | 8/1960 | Rupert . |
| 2,953,145 | 9/1960 | Moss et al. . |
| 3,271,786 | 9/1966 | Joy . |
| 3,368,575 | 2/1968 | Besonen . |
| 3,419,915 | 1/1969 | Clark, Jr. . |
| 3,875,596 | 4/1975 | Noda . |
| 3,889,698 | 6/1975 | Roessl . |
| 4,277,855 | 7/1981 | Poss . |
| 4,796,649 | 1/1989 | Tolomay ........................ 135/901 X |
| 5,117,481 | 5/1992 | Sung ............................... 4/526 X |
| 5,416,931 | 5/1995 | Wolfenden et al. ............. 4/526 |

FOREIGN PATENT DOCUMENTS

| | | | |
|---|---|---|---|
| 0300577 | 1/1989 | European Pat. Off. ............. 4/531 |
| 0048609 | 9/1986 | Switzerland ....................... 4/524 |

*Primary Examiner*—Charles E. Phillips
*Attorney, Agent, or Firm*—Price, Gess & Ubell

[57] ABSTRACT

A sauna fabricated from a tubular metal space frame mounting a circular plywood seat and shrouded by a vinyl and thermal shield skin having a clear plastic thermoformed hinged door therein with a magnetic door latch. A manually-actuated, timer-controlled electric infrared heater is located in a domical array in the top of the space frame assembly with the innermost dome serving as a reflector for the infrared heater.

18 Claims, 16 Drawing Sheets

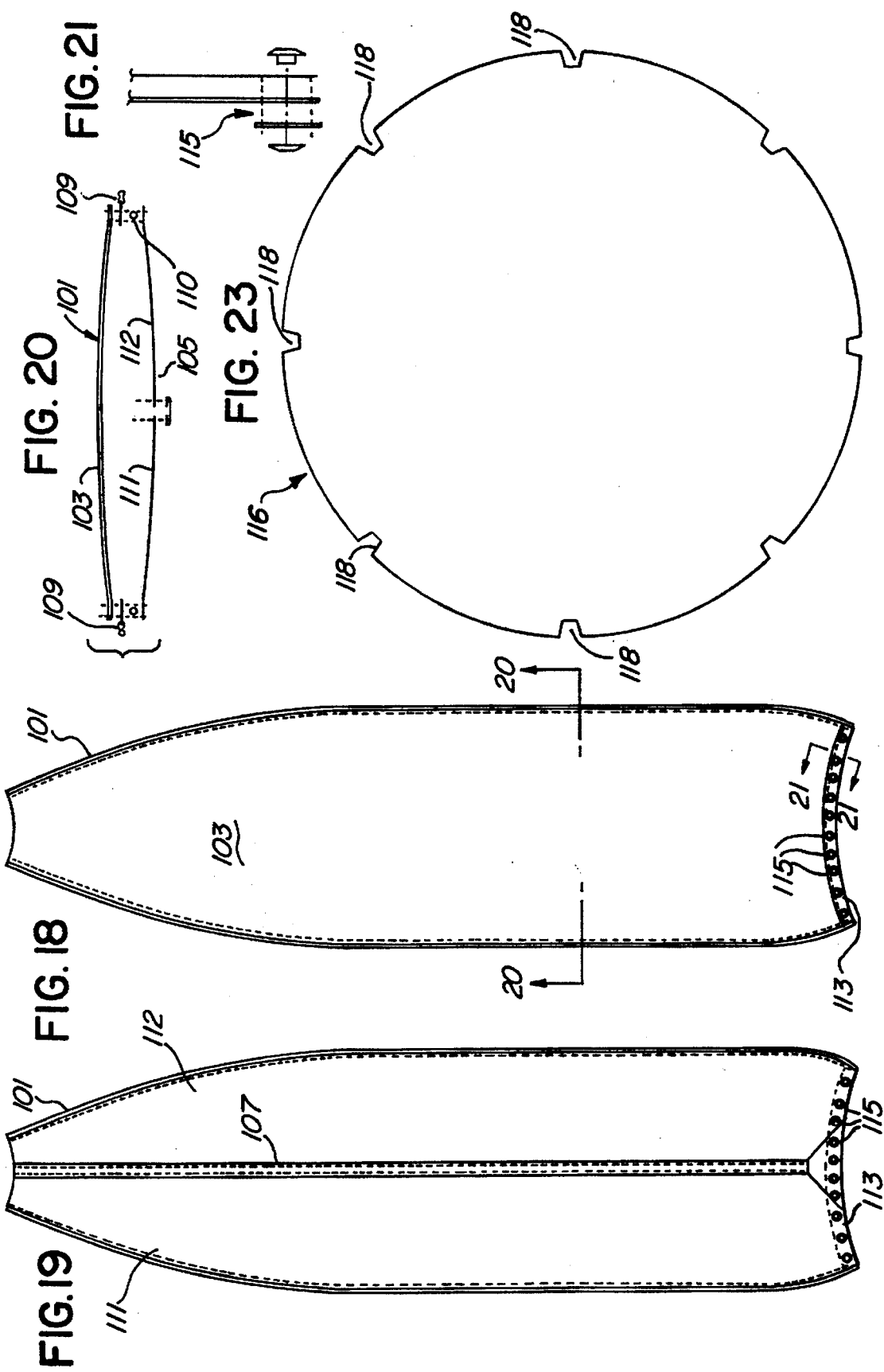

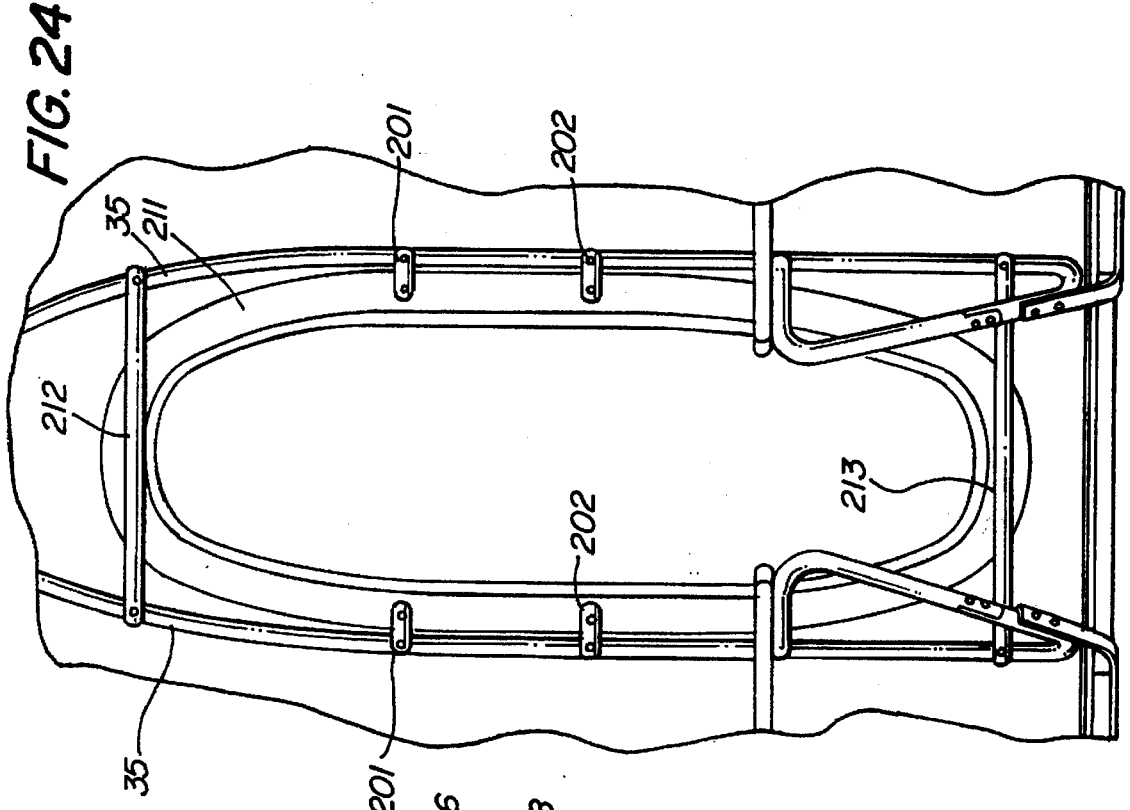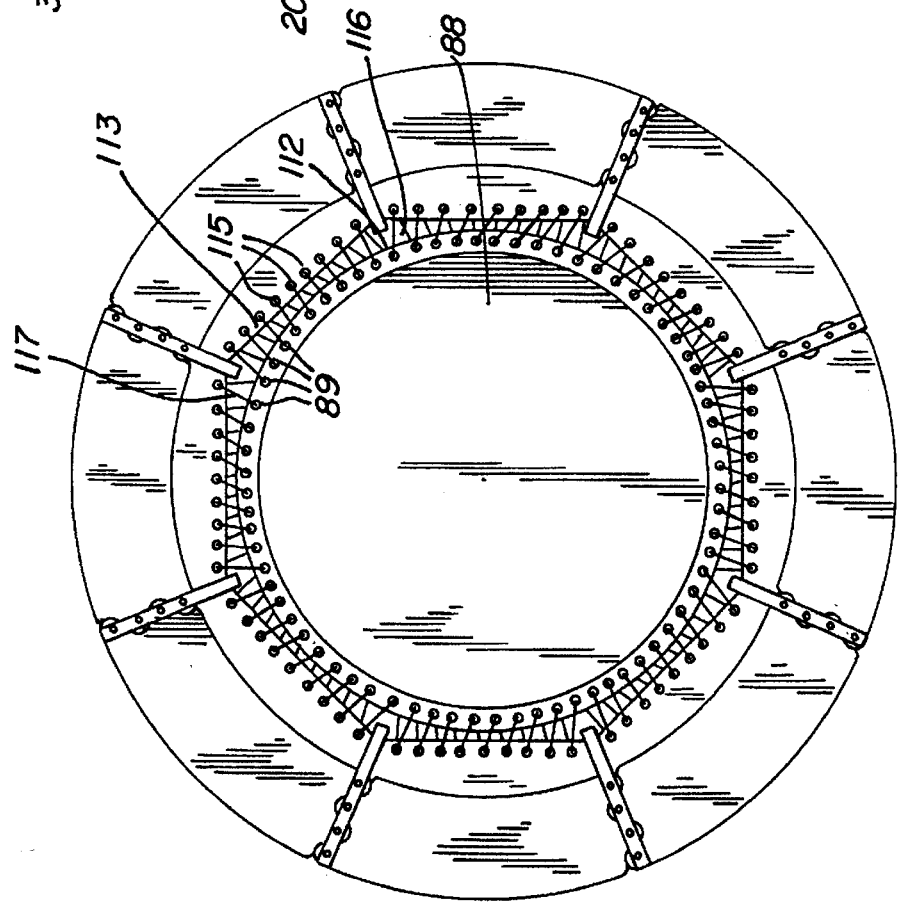

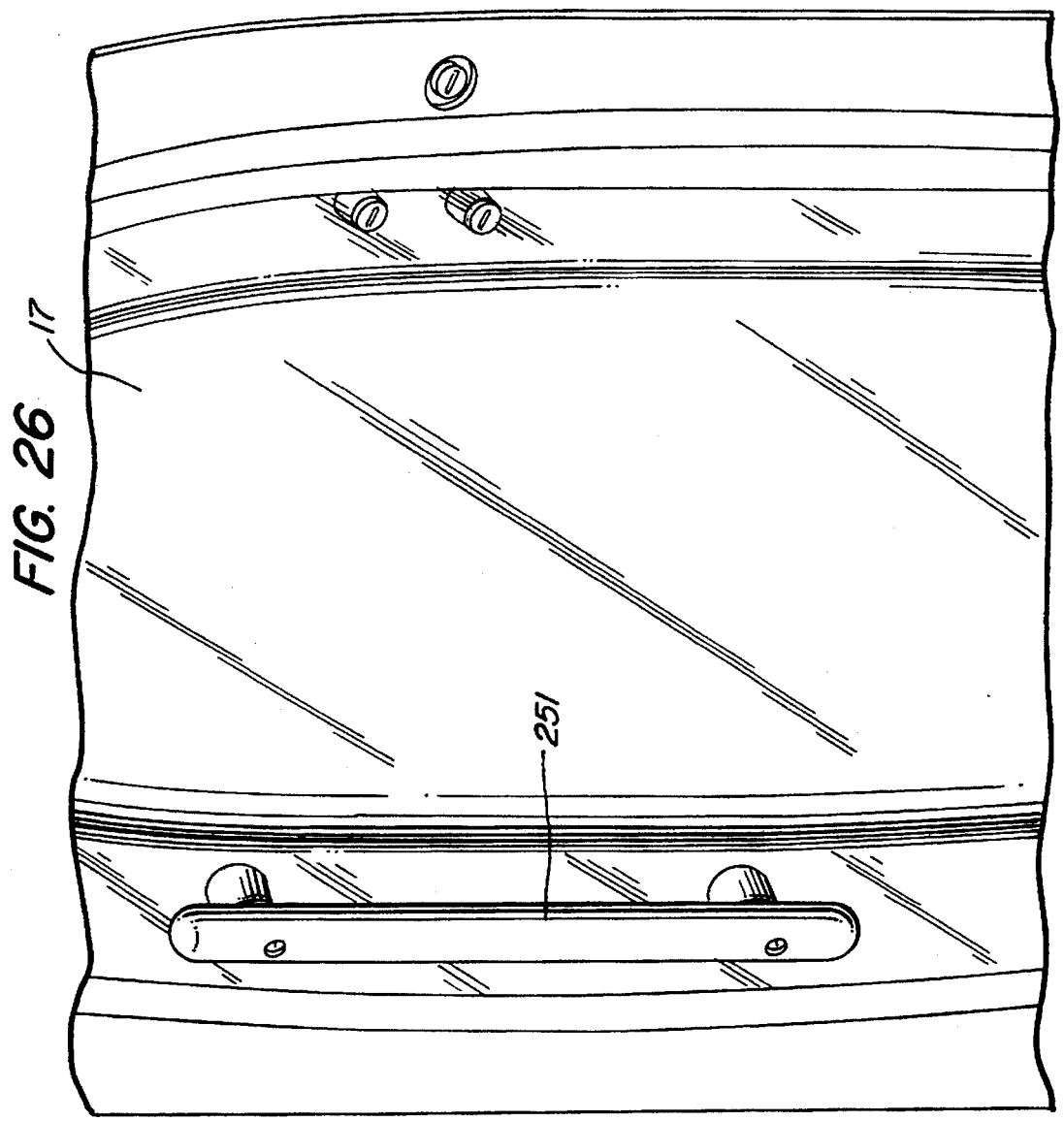

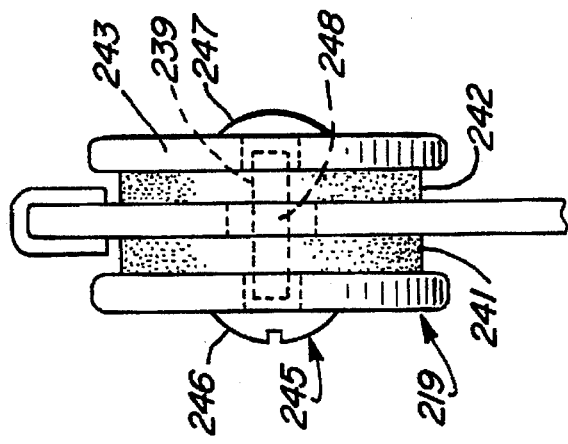
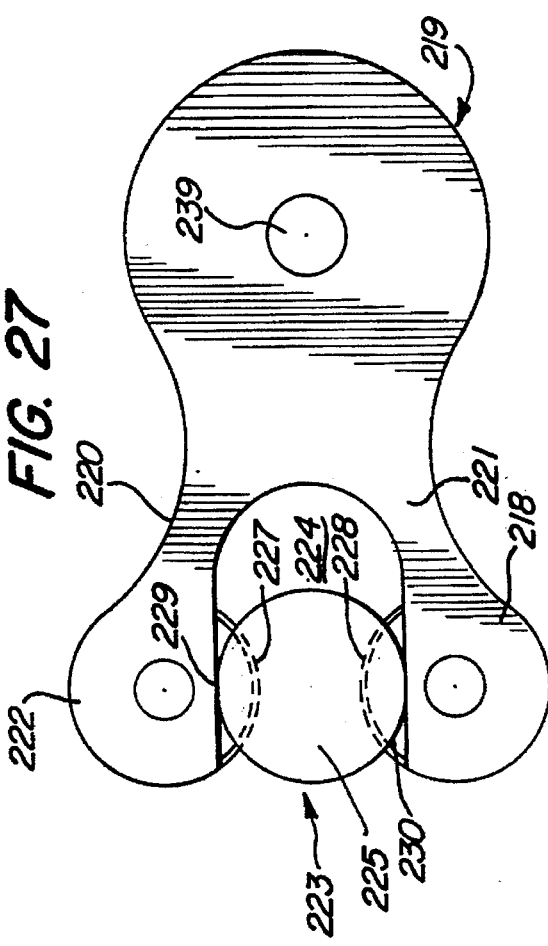
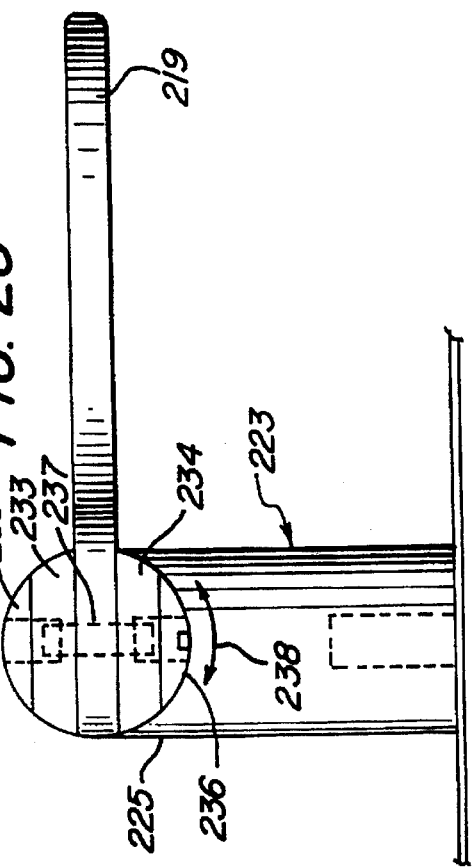

SAUNA

BACKGROUND OF THE INVENTION

1. Field of the Invention

The subject invention relates generally to saunas and, more particularly, to an improved sauna for consumer assembly and use.

2. Description of Related Art

Custom-built saunas are known in the prior art. Such saunas suffer a number of limitations. These limitations include the high initial cost of custom-built sauna rooms and long warm-up times.

Saunas have evolved which reduce these limitations by providing a free-standing unit that does not require assembly by a contractor and employs radiant heating for quicker warm-up. Such systems, however, weigh several hundred pounds, require significant warm-up time, are typically located indoors, and do not provide an effective thermal environment.

OBJECTS AND SUMMARY OF THE INVENTION

It is therefore an object of the invention to improve saunas;

It is another object of the invention to provide a user-assembled sauna;

It is another object of the invention to provide a lightweight portable sauna;

It is another object of the invention to provide a portable sauna with improved heating capabilities;

It is another object of the invention to provide a portable sauna which is inexpensive;

It is another object of the invention to provide a portable sauna which can be adapted to be indoor or outdoor installation; and It is another object of the invention to provide a portable sauna which meets UPS shipping requirements.

According to the invention, a sauna is fabricated employing a space frame structure constructed of arched tubes which are joined at the top into a dome structure. The dome structure accommodates an infrared heater system. In a preferred embodiment, the arched tube space frame structure includes a seat-mounting portion and feet for mounting a surrounding base element. In this embodiment, the space frame structure is covered with a stressed skin wherein an opening is provided for a hinged, magnetically latched transparent door. All of the components are readily removably attachable to one another to provide for user assembly and portability.

Saunas or dry heat appliances constructed according to the preferred embodiment may provide an attractive, comfortable, and effective thermal environment for four adults. In addition, such structures may warm up in approximately 30 seconds; plug into a standard 110-volt, 15-amp outlet, and weigh less than 150 pounds. Additionally, they can be UPS-shippable and provided to customers at an attractive price.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

FIG. 18 is a front view of a gore section of the preferred embodiment;

FIG. 19 is a back view of the gore section of FIG. 18;

FIG. 20 is a sectional view taken at 20—20 of FIG. 18;

FIG. 21 is a sectional view taken at 21—21 of FIG. 18;

FIG. 22 is a bottom view of the sauna of the preferred embodiment;

FIG. 23 is a top view of a lay-in component usable in the preferred embodiment;

FIG. 24 is a plan view of the inside of the door of the preferred embodiment;

FIG. 26 is an interior perspective view of a portion of the exterior door and door frame structure of the preferred embodiment;

FIG. 27 is a side view of a door hinge according to the preferred embodiment;

FIG. 28 is a top view of the hinge of FIG. 27;

FIG. 29 is a partial detail sectional view of the hinge-door attachment mechanism;

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a lightweight, easily assembled sauna structure.

Figure 1:
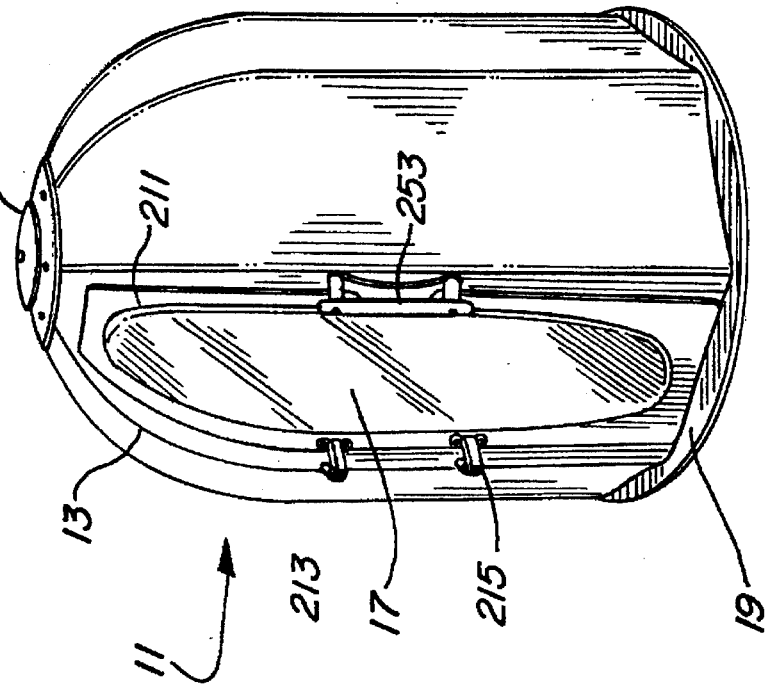
FIG. 1 a perspective view of a portable sauna according to the preferred embodiment.
Figure 4:
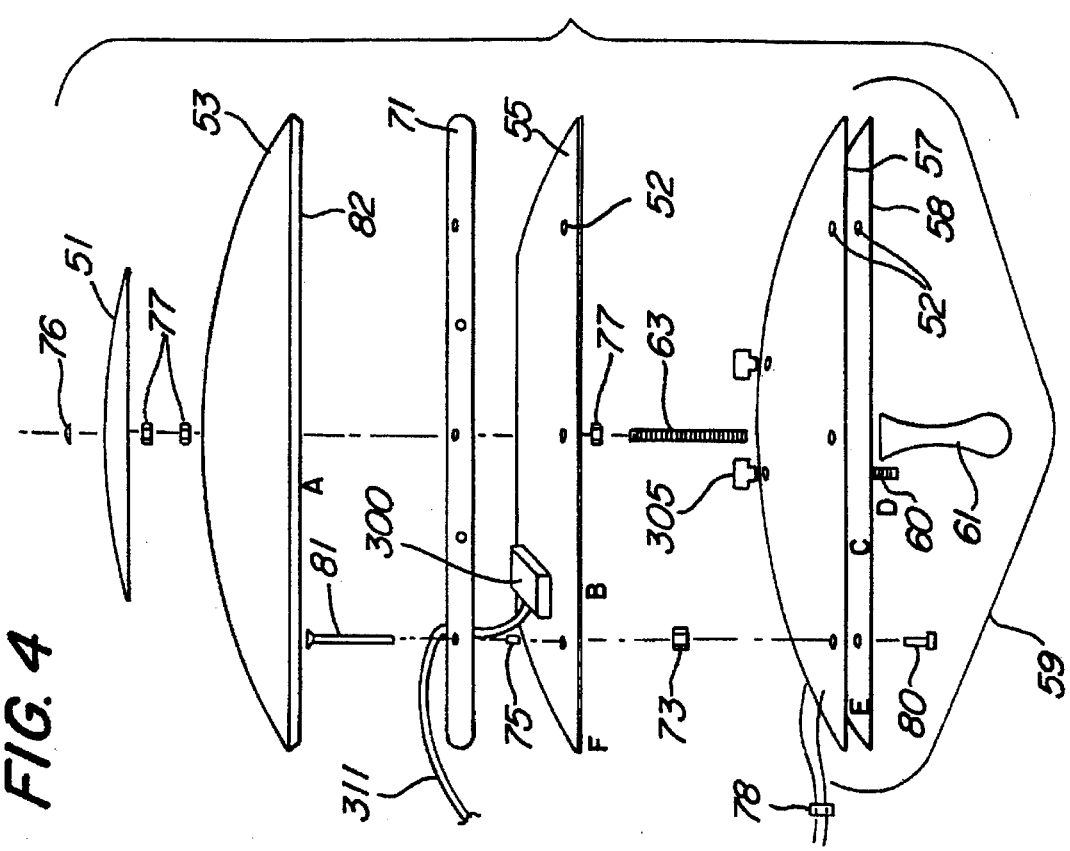
FIG. 4 is a side view assembly drawing illustrating a dome structure according to the preferred embodiment.

A sauna 11 according to the preferred embodiment is illustrated in FIG. 1. The sauna 11 is generally formed on a base 19 and includes an enclosure provided in part by a skin 13 having a heat-reflective inner surface. The skin 13 is supported by a frame structure 31 (FIG. 2) and terminates at its juncture with an upper dome structure 15 where it overlaps a halo ring 71 (FIG. 4). A transparent door 17 is provided to open and close in a frame 211 mounted to the frame structure 31. The preferred door 17 and hinge structure is described in detail in conjunction with subsequent figures.

Figure 2:
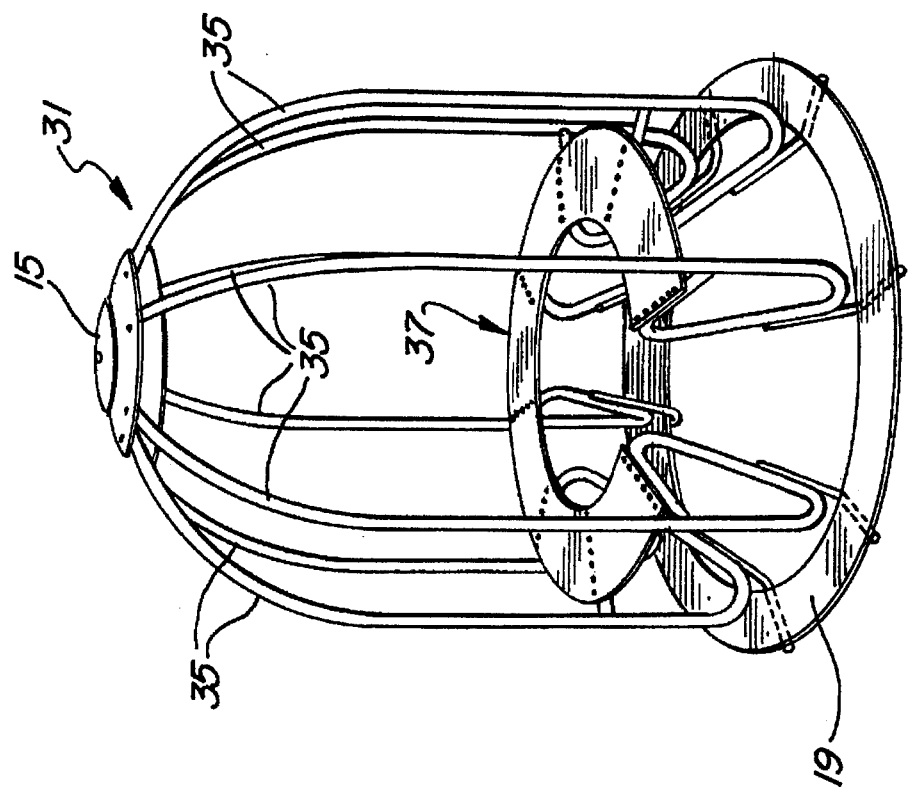
FIG. 2 is a perspective view illustrating a space frame structure according to the preferred embodiment.

The frame structure 31 illustrated in FIG. 2 comprises a metal tubing space frame comprising eight aluminum upwardly-extending arched tube members 35 arrayed in octal symmetry. The aluminum tubes 35 support a circular array of seats 37 and attach to the dome structure 15, as will be hereafter described in further detail.

Figure 3:
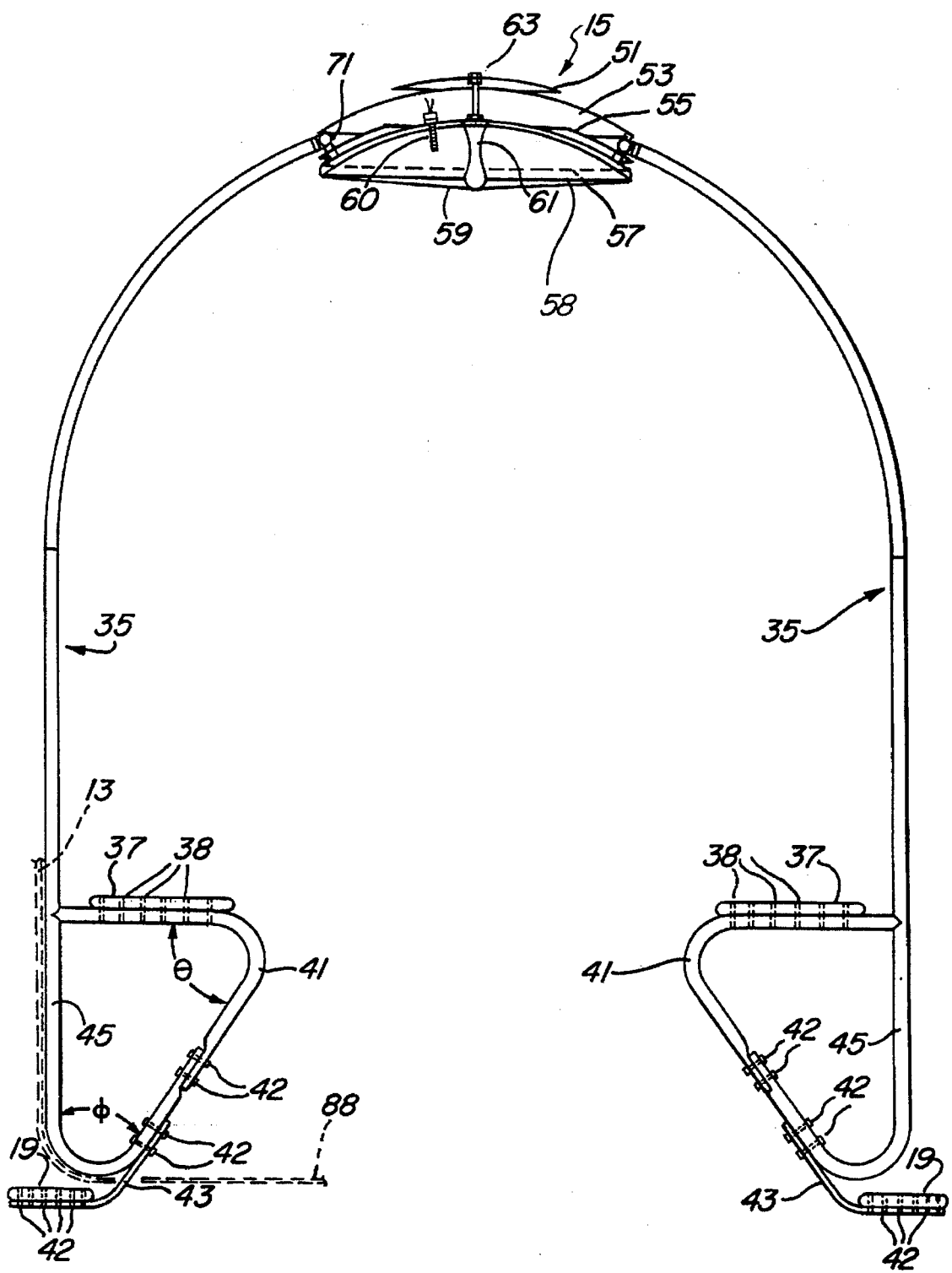
FIG. 3 is an elevational schematic view of the preferred space frame.

As illustrated in FIG. 3, each tube member 35 includes a seat support tube 41 which is bent through an angle $\theta$ of 53.1 degrees and a skin support tube 45 which is bent through an angle $\phi$ of 36.9 degrees. The skin support tube 45 is attached via fasteners 42 to the seat support tube 41. Corresponding feet 43, which are bent through an obtuse angle, are fastened via fasteners 42 to the inner end of each tube 45 and provide a pedestal to which the base 19 is fastened via suitable mechanical fasteners 42.

Figure 13:
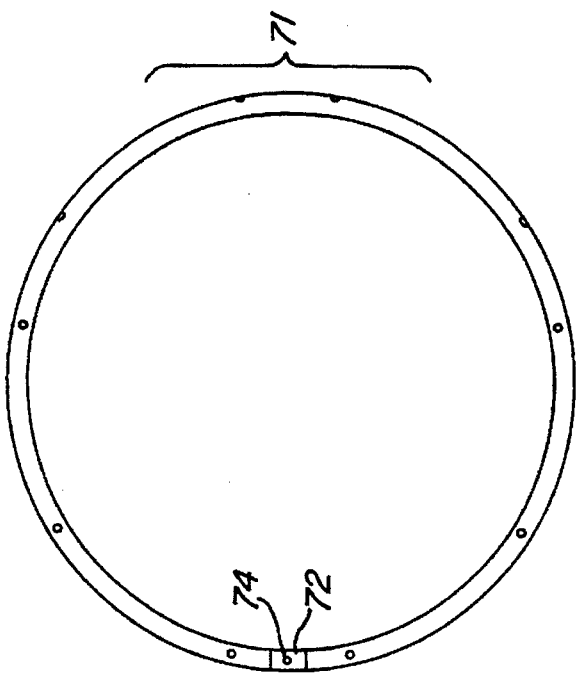
FIG. 13 a top view of a halo component according to the preferred embodiment.

FIGS. 3 and 4 further illustrate the construction of the dome structure 15 according to the preferred embodiment as including five domical elements 51, 53, 55, 57, 58, each of which may be fabricated of aluminum. The dome structure 15 is centrally held together by a threaded rod 63 which is threaded into a center post 61. The center post 61 spaces a protective wire mesh screen 59 away from infrared heating elements 60, which extend through the fifth and fourth domical elements 58, 57. The domical elements 53, 55, 57 are further held in spaced-apart relation at their respective edges by standoffs 73, 75. The standoff 75 abuts a halo ring 71, to which the upwardly-extending arched tube members 35 are attached by means of parachute fasteners 79 and suitable screws and nuts (FIG. 27). As may be further seen, a fastener 81 passes through the halo 71 and is threaded through the standoff 75 and into the standoff 73 to hold the structure together. A seal 82 is provided along the perimeter between the outer edge of the dome 53 and the halo 71 to capture the skin and to reduce wind and precipitates. FIG. 13 illustrates a top view of the halo 71, which, as noted, holds the dome structure and the tube structure together to form a space frame and includes a nylon plug 72 having a hole 74 therein through which electrical power cabling may pass.

Figure 5:
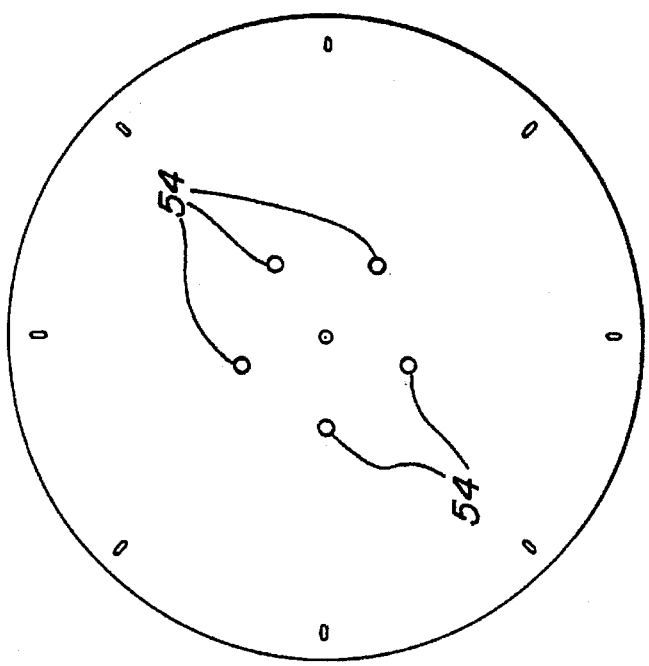
FIGS. 5–12 top and side views of various domical elements of FIG. 4.
Figure 6:
Figure 32:
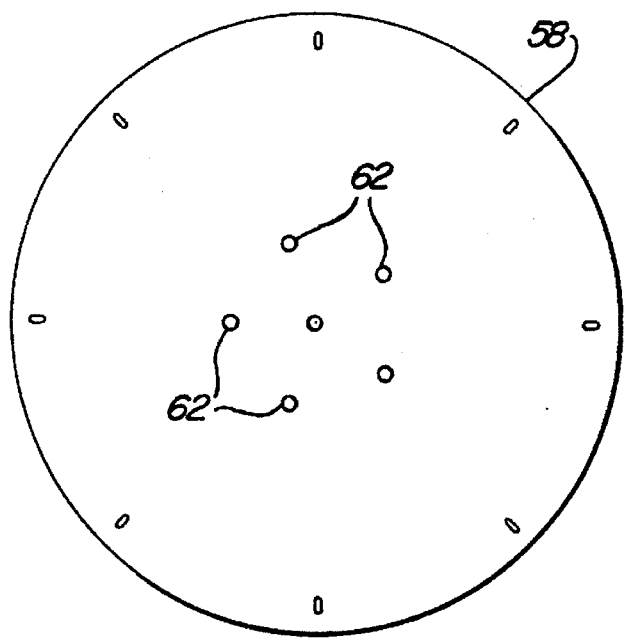
FIGS. 32 and 33 are respective top and side views of a fifth domical element of the dome structure illustrated in FIG. 4.
Figure 33:
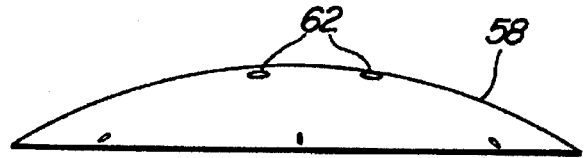

FIGS. 5–10 and 32–33 illustrate further details of the domical elements 51, 53, 55, 57, 58. FIGS. 5–6 particularly illustrate a number of mounting holes 54 present in the dome structure 57 for mounting five silicon carbide infrared heater elements 60. FIGS. 32–33 illustrate holes 62 in the innermost dome structure 58 through which the heating elements 60 pass. Making the downwardly-facing surface of the innermost dome 58 solid promotes development of a stable air space or air mass about the heater elements 60.

Figure 7:
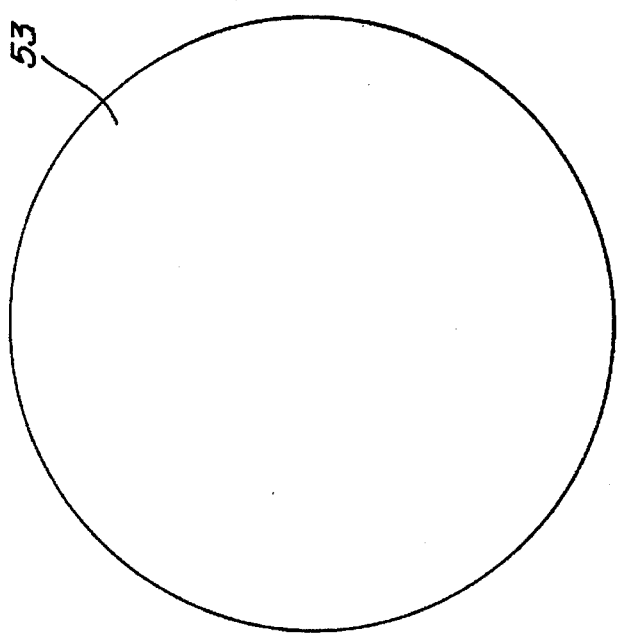
Figure 8:
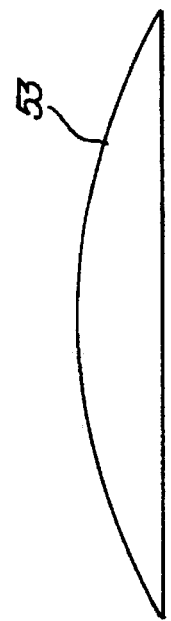
Figure 9:
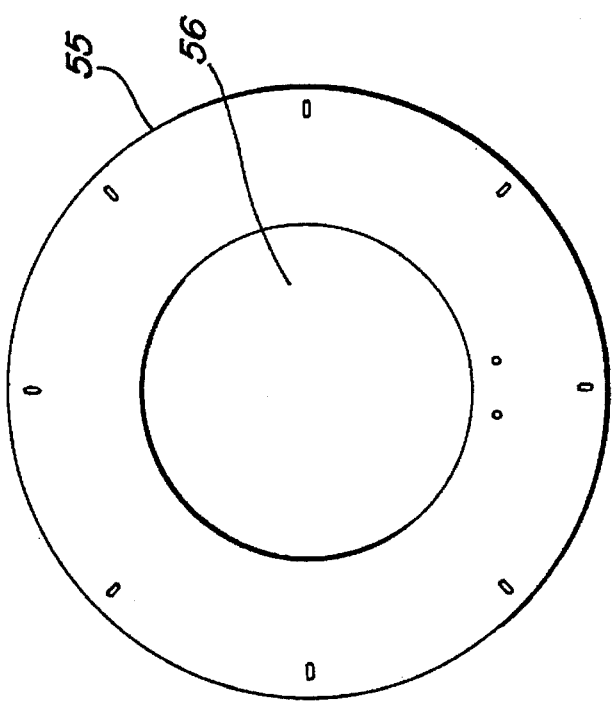
Figure 10:
Figure 11:
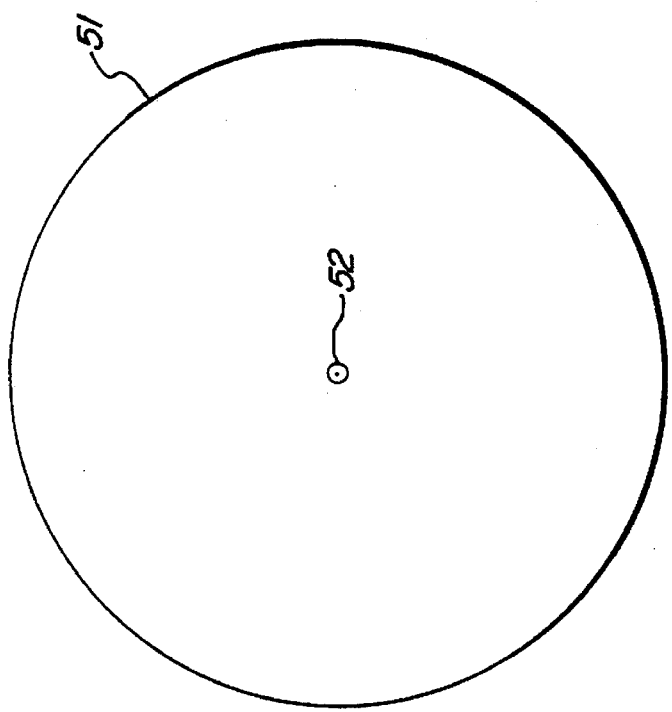
Figure 12:

FIGS. 7 and 8 show the generally truncated dome shape of the domical element 55 and the central circular opening 56 therein, which provides heat convection/conduction. FIGS. 9 and 10 illustrate the domical element 53. Finally, as may be seen with reference to FIGS. 11 and 12, the outer domical element 51 is an entirely solid surface with the exception of a central hole 52 for mounting the threaded rod 63 or other fastening mechanism. While the preferred embodiment employs five domical elements, various other dome structures having various numbers of domical elements fabricated of various materials including stainless steel could be provided without departing from the scope and spirit of the invention.

The preferred embodiment employs natural convection by allowing air currents to enter the unit in the floor region and flow upward and eventually outward through the dome structure 15 at the top of the enclosure. A design consideration in the preferred embodiment is the amount of heat transferred from the domical elements 51, 53, 55, 57, 58 into the surrounding structure, which may cause the halo 71 to become so hot as to melt the vinyl skin 13. Thus, the standoffs 73, 75 are provided to open up the dome structure 15 and to provide convection currents which naturally cool each one of the domical elements 51, 53, 55, 57, 58.

Figure 14:
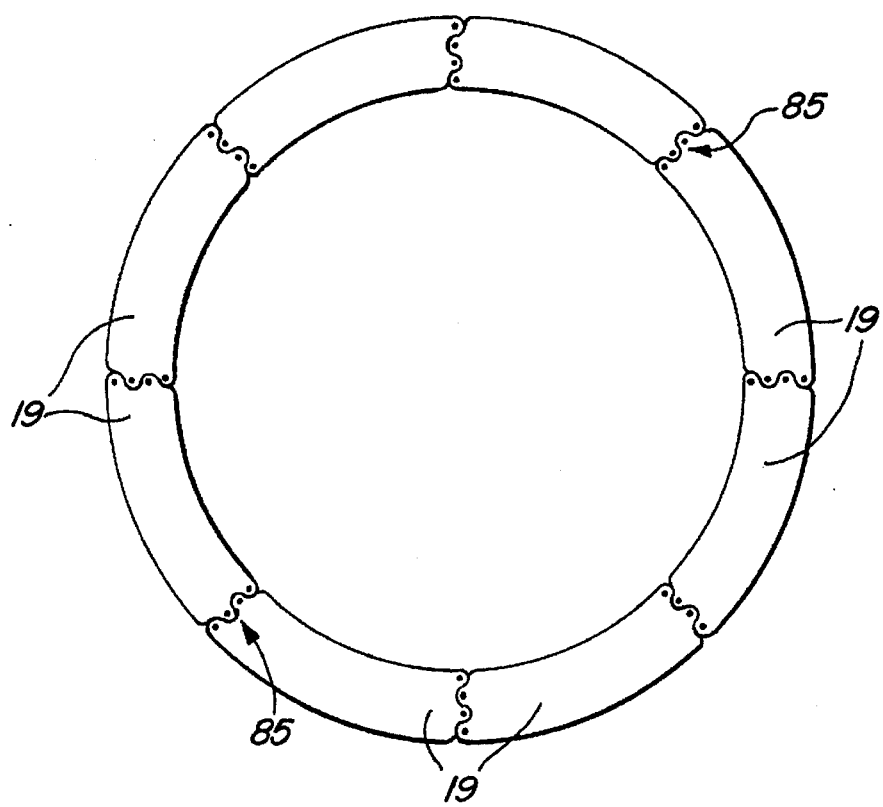
FIGS. 14 and 15 are top views illustrating base and seating structure according to the preferred embodiment.
Figure 15:
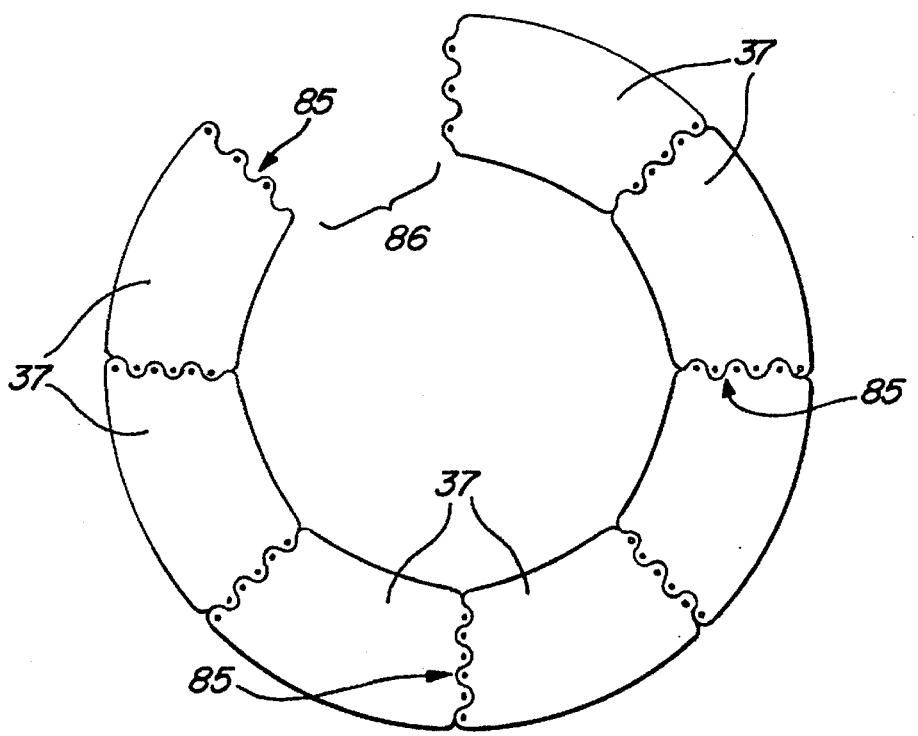

FIGS. 14 and 15 show a top view schematically illustrating the structure of the seat members 37 and interlocking base members 19. These members 19, 37 may be fashioned of wood, for example, Finland birch plywood, and provided with interlocking fingers 85 at their intersections. The interlocking fingers 85 are fastened to a common support member, e.g., seat tubes 41 and feet 43 by mechanical fasteners disposed normally through each finger 85. Thus, a relatively stiff structure results after assembly by the user, while still providing for removal of the individual seats 37 and bases 19 for packing. An opening 86 is provided in the circular array of seats 37 where the door 17 in the outer skin 13 is located.

Figure 17:
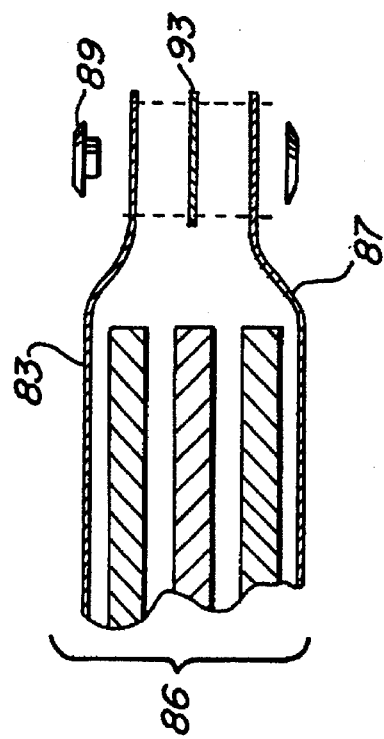
FIG. 17 is a sectional view taken at 17—17 of FIG. 16.
Figure 16:
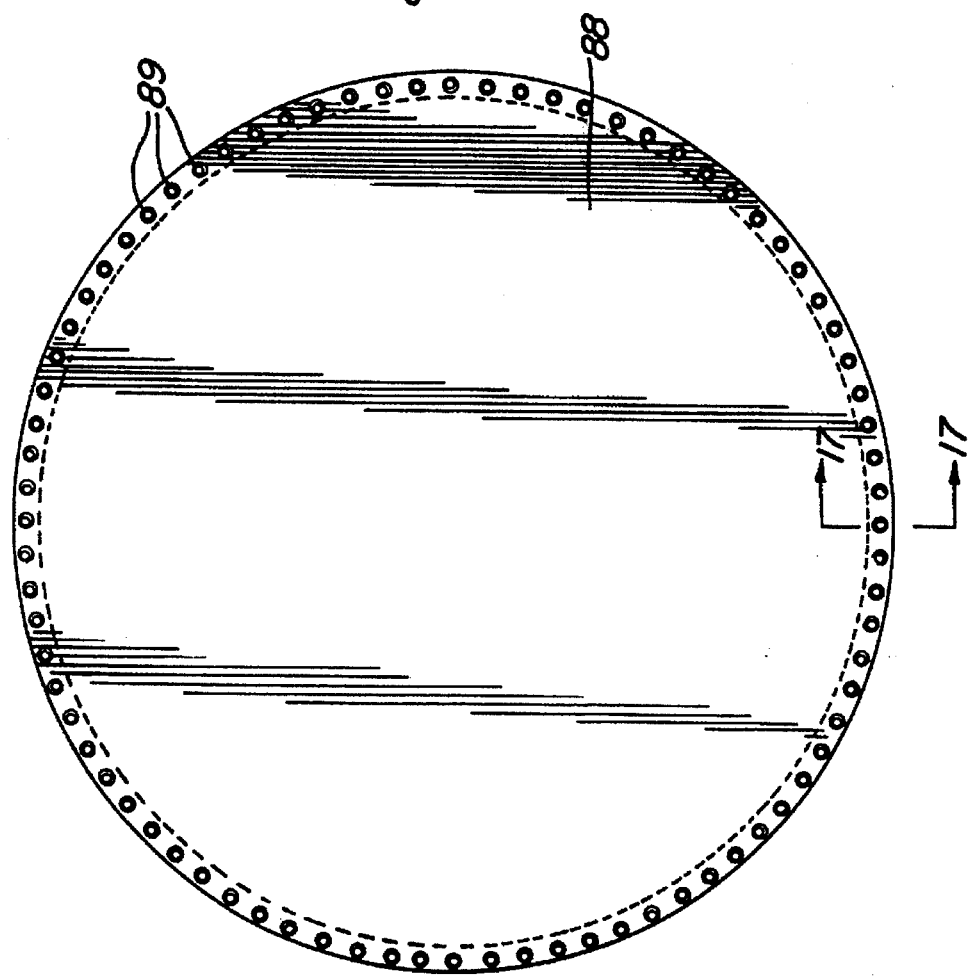
FIG. 16 is top view of a portable sauna floor according to the preferred embodiment.

FIGS. 16 and 17 illustrate a floor 88, which may be located in the interior of the sauna 11 beneath the seats 37 for user comfort. As seen in FIG. 16, the floor 88 may include upper and lower vinyl covering layers or sheets 83, 87 and an inner insulative layer 86 such as foam provided between the upper and lower coverings 83, 87. The edges of the respective vinyl sheets 83, 87 are sewn together and a number of grommets 89 installed at equal intervals around the circumference of the floor using nylon tape 93.

FIGS. 18–20 illustrate the construction of a wall panel or skin section 101, eight of which are attached together by zippers 109 along their vertical edges to form the stressed skin composite or outer skin 13. As best shown in FIG. 20, the skin section 101 includes an outer surface 103 and an inner surface 105. The outer surface 103 is preferably formed of marine vinyl, while the inner surface 105 is formed of two sections 111, 112 of reflective rip stop nylon thermal shield joined together by a vertical strip 107 of an elastic material such as Spandex.

The outer marine vinyl fabric 103 expands upon heating and contracts upon cooling. As noted, the inner fabric 105 is a rip stop nylon thermal shield, which may have one surface aluminized and overcoated with a clear urethane. This material shrinks upon heating and expands upon cooling. To maintain attractive appearance of the fabric, the inner fabric 105; that is, the rip stop nylon, is composed of two bias cut elements, and provided with the bridging strip 107 made of an elastic material, which serves as a spring or elastic element to help the inner material remain taut during changes in temperature. The outer skin 13 is thus sufficiently taut when assembled over the frame 31 that it does not require fastening either to the frame 31 or to the dome 15, except preferably at the doorway by wrapping the skin 13 around the edge of the doorway frame 211 (FIG. 24) and holding it in place, e.g., by a deformable plastic trim element.

As seen in FIGS. 18, 19, and 21, the bottom edge 113 of the outer skin 101 has a plurality of grommets 115 formed therein which cooperate with corresponding grommets 89 to provide a mechanism to fasten the floor 88 to the bottom edge 113 of the portable sauna outer skin 13. As seen in FIG. 22, this mechanism is completed by lacing 117, which interconnects the grommets 89, 115 about the entire periphery or circumference of the floor 88. Equally-spaced grommet holes, e.g. 24–80 in number, are preferably provided. By providing a selected gap between the edge 113 and the circumference 112 of the floor 88, air entry is facilitated, a means for permitting the feet 43 to protrude is provided, and the lacing 117 can be tightened so as to impart tension to the skin 13. Tensioning prestresses the skin 13, the floor membrane 88, and the frame tube structure 31. The prestress helps to maintain a taut skin 13, while allowing reasonable part tolerances, temperature cycling, and aging.

Also visible in FIG. 22 is a vinyl lay-in 116 shown in more detail in FIG. 23, which covers the gap between the floor circumference 112 and the edge 113, and thus assists in keeping out excessive air entry due to wind. The lay-in 116 has suitable cutouts 118 to accommodate the frame tubing.

The skin 13 serves as a seat back for the users who typically position themselves between the structural members 35. The tubes 35 may themselves be "skinned"to present a more comfortable surface to users, to provide compliance between the structure 31 and the skin 13 via elastic or plastic deformation, and/or to help provide an effective weather seal at gore interconnections. Such a tube skin may comprise a layer of polymer foam covered with a fabric sock having a long wavelength infrared reflective exterior. Reflective media in the sauna interior may be terminated at or just below seat height.

With respect to the manner of joining individual skin sections 101, as an alternative to sewing, the sections 101 may be thermoplastically fused together at the edges by induction heating, direct electrical contact, or mechanical contact with a heat source. Means may further be provided to align the gores or sections 101 with the frame tubes 35. Such means may comprise ⅛-inch piping 110 as shown in FIG. 20 along the gore edges, which effectively creates two notches, one on either side of the zipper 109. Piping may thus be used at the gore edges to aid in aligning the gores 101 with the frame structure 31.

Zipper strips 109 for joining the skin sections 101 may be attached in various manners, such as via thermosetting hot melt adhesive; double-sided foam, film-supported adhesives; transfer adhesives; and dry film adhesives. An air/water seal may be provided about the zippers 109 via silicone grease, underlapping fabric, interior material strips which cover the tubes 35, and various other mechanisms. Commercially-available "zip strips"may also be used to provide a watertight seal. Additionally, the gores 101 may be connected by means other than zippers such as webbing or elastic intermediate elements employed at some or all of the joints. Skin laminates, e.g., 103, may further include insulative spaces containing air, nonwoven fibrous mats, polymer foam, netting, screens, or metallic films. Skin laminates, e.g. 103, themselves may be "connected," i.e., initially made in reel-to-reel processes, and then separated for assembly.

Frame elements such as tubes 35 may also be extruded with grooves to facilitate the attachment of the gores 101 at gore junctions. Gore edges may be cut or otherwise manufactured in a sinusoidal pattern to minimize the need to align them with the frame elements 35 and to spread tensile loads over a larger length.

As an alternative to employing skin sections 101, the sauna skin 13 itself may comprise a custom knitted unitary sock. Colors and patterns can be integrated into the fabrics. The flammability of an expanded vinyl outer skin may be reduced by infusing the materials' voids with baking soda.

The sauna door 17 conforms to the opening and side profile of the outer skin 13, and thus has a side profile which extends generally upward and then arches over. The door 17 is fabricated of a thermoformed transparent plastic such as polycarbonate such that persons occupying the sauna are able to see out of the sauna, helping to alleviate claustrophobia. The door 17 preferably has a protective trim mounted around its peripheral edge, which seals with a foamed elastomer or similar sealing material installed around the peripheral edge of the generally elliptical door frame 211.

Attachment of the door frame 211 to the sauna structure is illustrated in the interior view of FIG. 24. As shown, a pair of aluminum side braces 201,202 fasten the respective sides of the frame 211 to respective upwardly-extending arched tube members 35. An upper aluminum cross-brace 212 and a lower aluminum cross-brace 213, which may be, for example, one-inch-diameter tubes, are also fastened to the respective tube members to the bottom and top horizontal portions of the door frame 211, respectively. The door frame 211 itself may be fabricated of inner and outer aluminum layers or skins sandwiching a polyethylene layer and designed to be of sufficient strength to resist bowing. The frame attachment mechanism should provide stable and secure positioning of the frame 211. A variety of door frame and frame attachment structures can be constructed without departing from the scope and spirit of the invention. In addition, the door 17 may be hinged directly to the space frame structure, for example, to tubes 35 in alternate embodiments.

The thickness of the door 17 is preferably 3/16-inch to lend desired stiffness and rigidity. As shown in FIG. 1, the door 17 is attached to the frame 211 by first and second hinges 213, 215, which are preferably constructed of aluminum according to the design shown in FIGS. 27–29. Various other hinge designs employing various commercially-available or custom hinge components may, of course, be utilized without departing from the scope and spirit of the invention.

The hinge 213 of FIGS. 27–29 includes a hinge piece 219 and a hinge rod 223, which are preferably constructed of aluminum. The hinge piece 219 includes an upper arm 220 and a lower arm 221, each of which disposes a spherically-shaped end portion 222, 223 in vertically-spaced-apart relation to one another about a gap 224. The extended end 225 of the hinge rod 223 has respective spherically-shaped depressions 227, 228 located on its upper and lower sides 229, 230. These depressions 227, 228 are sized to receive and mate with the spherically-shaped ends of the hinge piece 219.

The spherically-shaped ends of the hinge piece 219 are themselves each constructed of a plurality of components including first and second hinge knobs 233, 234 and first and second cap nuts 235 and 236. The hinge knobs 233, 234 have spherically-contoured outer surfaces to contribute to the overall spherical shape of end portions 222, 223.

To install the hinge piece 219 on the hinge rod 223, the hinge piece 219 is placed in the position shown, with the hinge knobs 233, 234 and cap nuts 235, 236 initially removed. The hinge knobs 233, 234 are then put in place on either side of the upper and lower arms 220, 221 and the cap nuts 235, 236 installed and threaded onto an internal threaded stud 237 to thereby hold the hinge knobs 233,235 in place. Once the respective pairs of hinge knobs 233, 234 are fastened in place in the respective spherical depressions 227, 228, the hinge piece 219 is effectively attached to the hinge rod 223 and can then only pivot in a horizontal plane, as reflected by the arrow 238 in FIG. 24. The hinge knobs 233, 234 are preferably black-colored nylon, while the cap nuts 235, 236 may be steel having tapped female portions threaded onto a ¼-inch stainless steel internal stud 237.

FIG. 29 illustrates the attachment of the hinge piece 219 to the door via a central hole 239. The attachment mechanism employs an internal and an external rubber washer 241,242 located on the interior and external surfaces of the door 17, an internal aluminum disc or washer 243, and a fastening device 245. The fastening device 245 may again comprise two cap nuts 246, 247 attached to an internal ¼-inch threaded stud 248.

Figure 25:
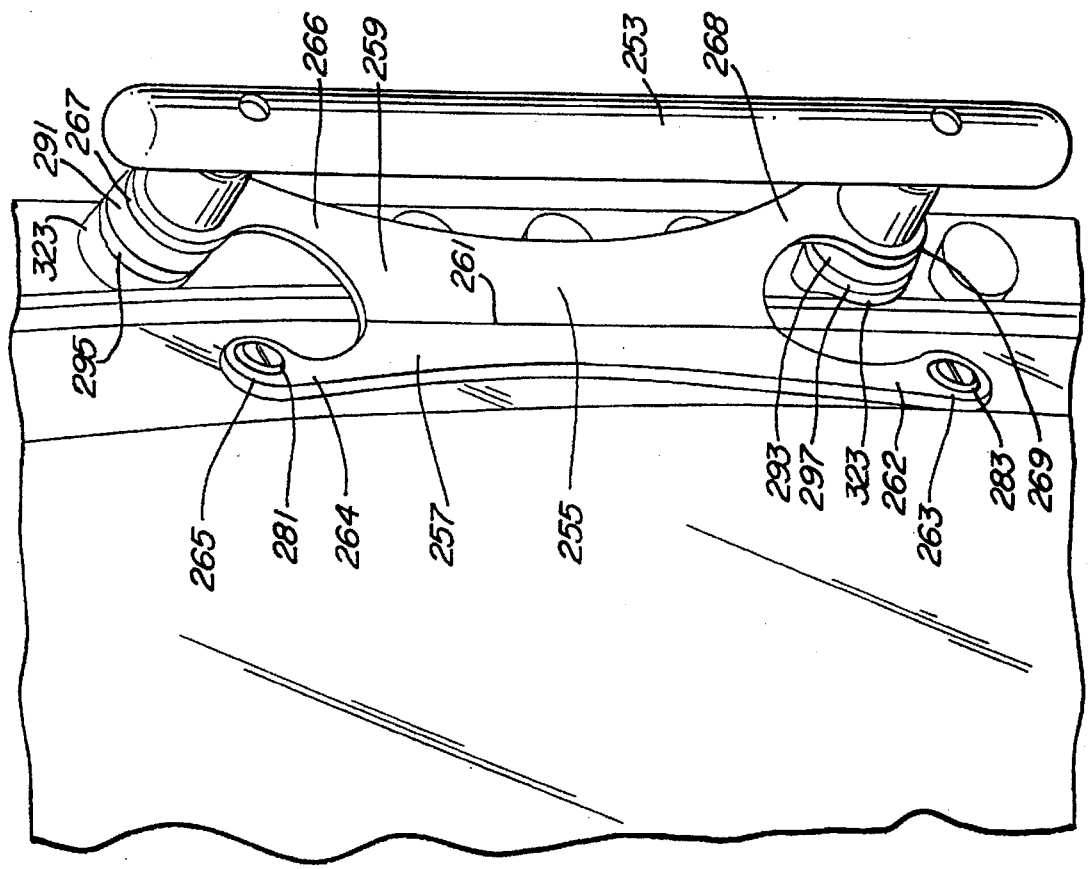
FIG. 25 is a side perspective view of a portion of the exterior door and door frame structure of the preferred embodiment.

An inside handle 251 (FIG. 26) and an exterior handle 253 (e.g. FIG. 25) are also attached to the door 17. The handles 251, 253 may comprise acrylic, nylon, or other plastic rods. The exterior handle 253 is attached to the door by a handle plate 255 having a left half 257 and a right half 259, which meet at an angle along a linear edge 261. The angle is selected to again accommodate the curvature of the door 17 and door frame 211 so as to suitably position mounting flanges 263,265, 267, 269 with respect to the door 17 and the door frame 211. The mounting flanges 263,265,267, 269 are positioned on respective winged extensions 262, 264, 266, 268, which extend from the central body portion of the handle plate 255. The handle plate 255 is preferably a unitary aluminum member, although it could be fabricated of various other materials.

Figure 30:
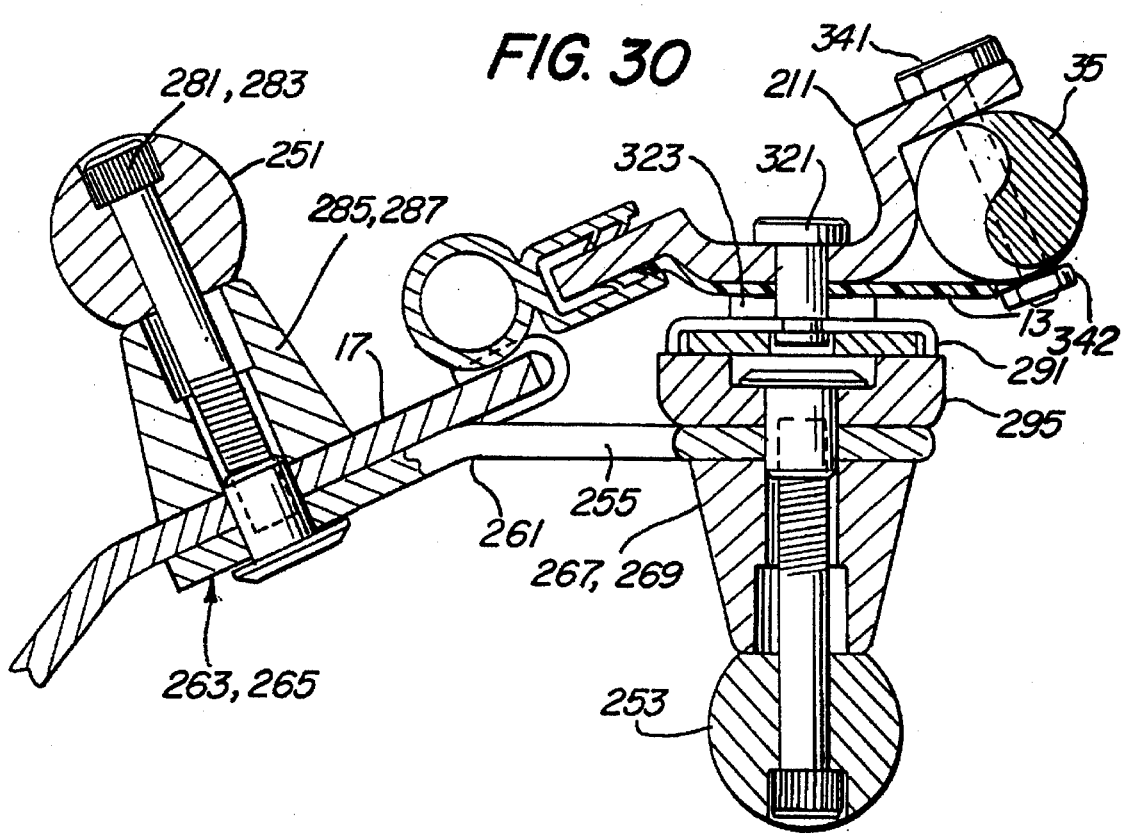
FIG. 30 is a partial sectional view illustrating part of a door latching mechanism according to the preferred embodiment.
Figure 31:
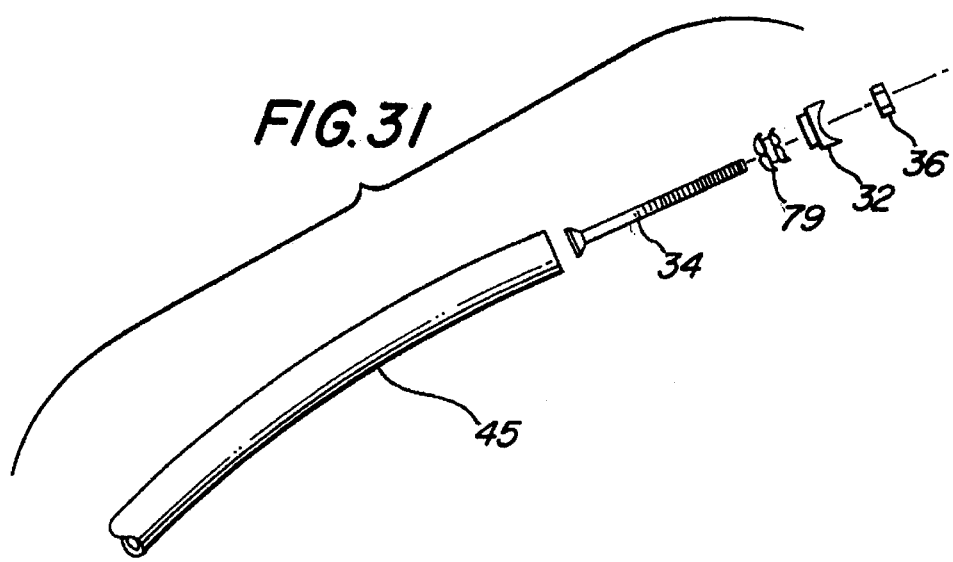
FIG. 31 is a partial exploded side view frame assembly drawing.

As seen, for example, in FIG. 30, suitable fasteners 281,283 extend through holes in the door mounting flanges 263,265 through spacers 285,287 mounted on the interior of the door 17, and finally through respective bores in the inner door handle 251 to fasten both the inner door handle 251 and the handle plate 255 to the door 17.

The winged mounting flanges 267, 269 extend outside the periphery of the door 17 and serve to position respective disc-shaped metallic door strikes 291,293 to engage respective magnets 295, 297 fastened to the door frame 211. The magnets 295, 297 may each comprise a ceramic disc magnet bonded into a nickel-plated steel pot, as commercially available, and the door strikes 291, 293 are generally cylindrical magnetic stainless steel. Suitable center holes are, of course, provided to facilitate mounting the magnets 295,297 and strikes 291,293 by suitable mechanical fasteners, e.g. 321. The magnetic susceptibilities or polarities are such that the magnets 295, 297 and respective door strikes 291,293 attract one another.

The magnetic hinge mechanism just described is employed to provide secure latching of the door 17, while still permitting it to be opened from the inside by merely pushing on the interior handle 251 or on the inside surface of the door 17. Also, the magnets 295,297 include a threaded screw 321 (FIG. 30) having a rubber washer 323 mounted between the magnets 295, 297 and the frame 211. A portion of each magnet 295,297 meets the rubber washer 323 such that each magnet 295, 297 may nutate or rotate slightly normal to the axis of the screw 321 to provide accommodation for tolerances. Fasteners such as screws 341 and nuts 342 are provided at intervals around the door frame 211 to attach the door frame 211 to ribs 35 on either side of the frame 211.

The magnetic latch means employed for latching the door 17 to the frame 211 can accommodate variations in door-to-structure positioning. The interior of the door 17 may be covered with a visibly transparent, long wavelength reflective coating to improve thermal efficiency. A privacy curtain may also be included to allow users to cover the inside of the transparent door 17.

Figure 35:
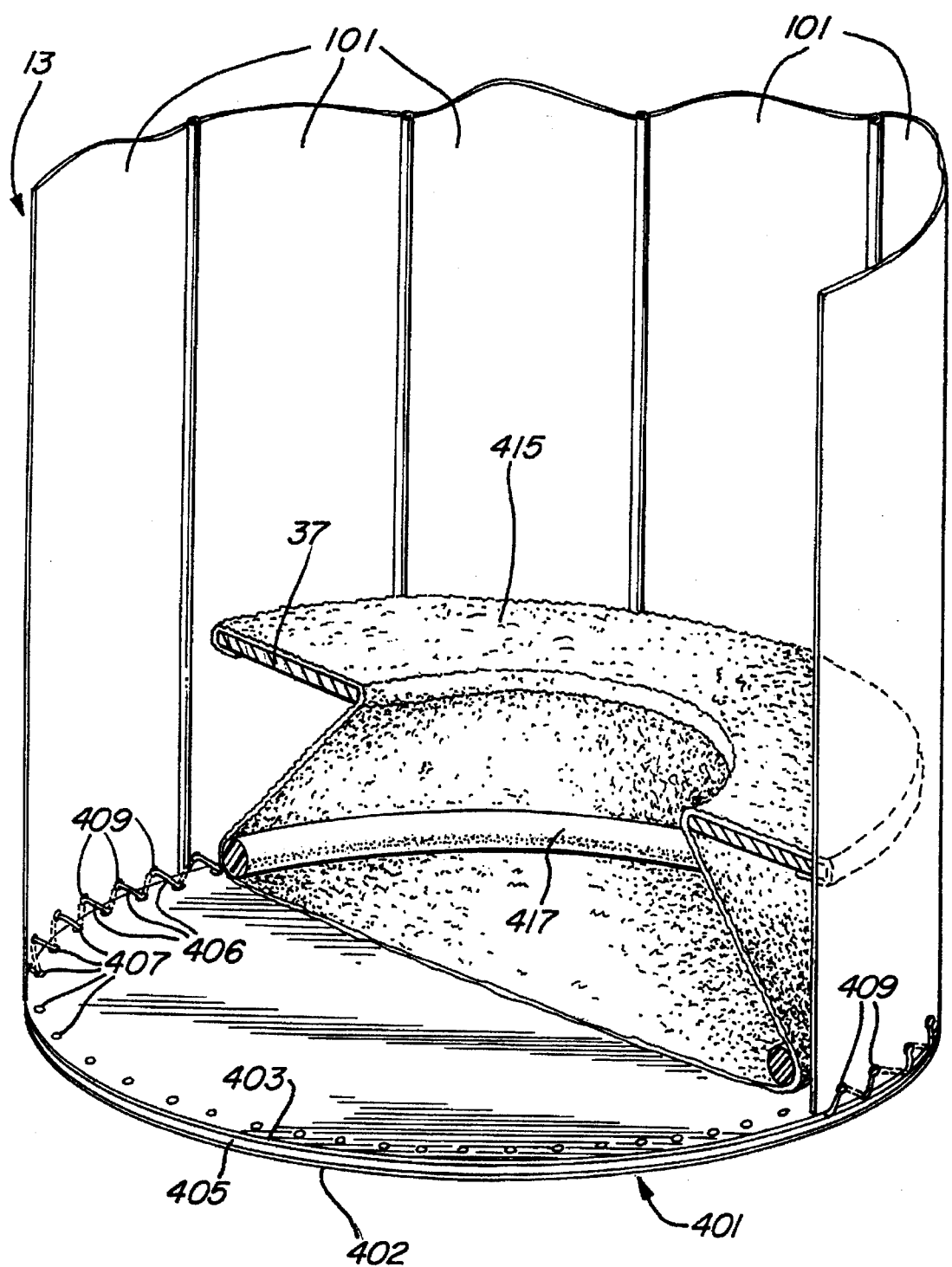
FIG. 35 is a partial perspective view illustrative of toweling employed in the preferred embodiment.

As illustrated in FIG. 35, the lower interior region of the sauna 11 is preferably covered by toweling 415 to provide a means to absorb perspiration, cushion the seats 37, reduce heat losses, and to enhance the look of the interior. Thus, the seats 37 and the lower interior region of the sauna 11 may be covered by the complex-shaped, easily removable towel member 415 which attaches to the seat array by an elastic tensile member in a means analogous to a fitted sheet. Additionally, hook-and-loop fasteners may be used to further secure the towel member 415 to the seats. Such toweling 415 is thus easily removable and launderable.

The towel member 415 is further preferably held outwardly against the structural tubes just above the floor by a circular compression member 417. This member 417 may be made from one-inch-diameter poly- butylene tubing joined at its ends by a tapered nylon plug to allow easy removal and installation of the toweling 415. Additional securing of the toweling at the doorway is preferably provided by stays.

Figure 34:
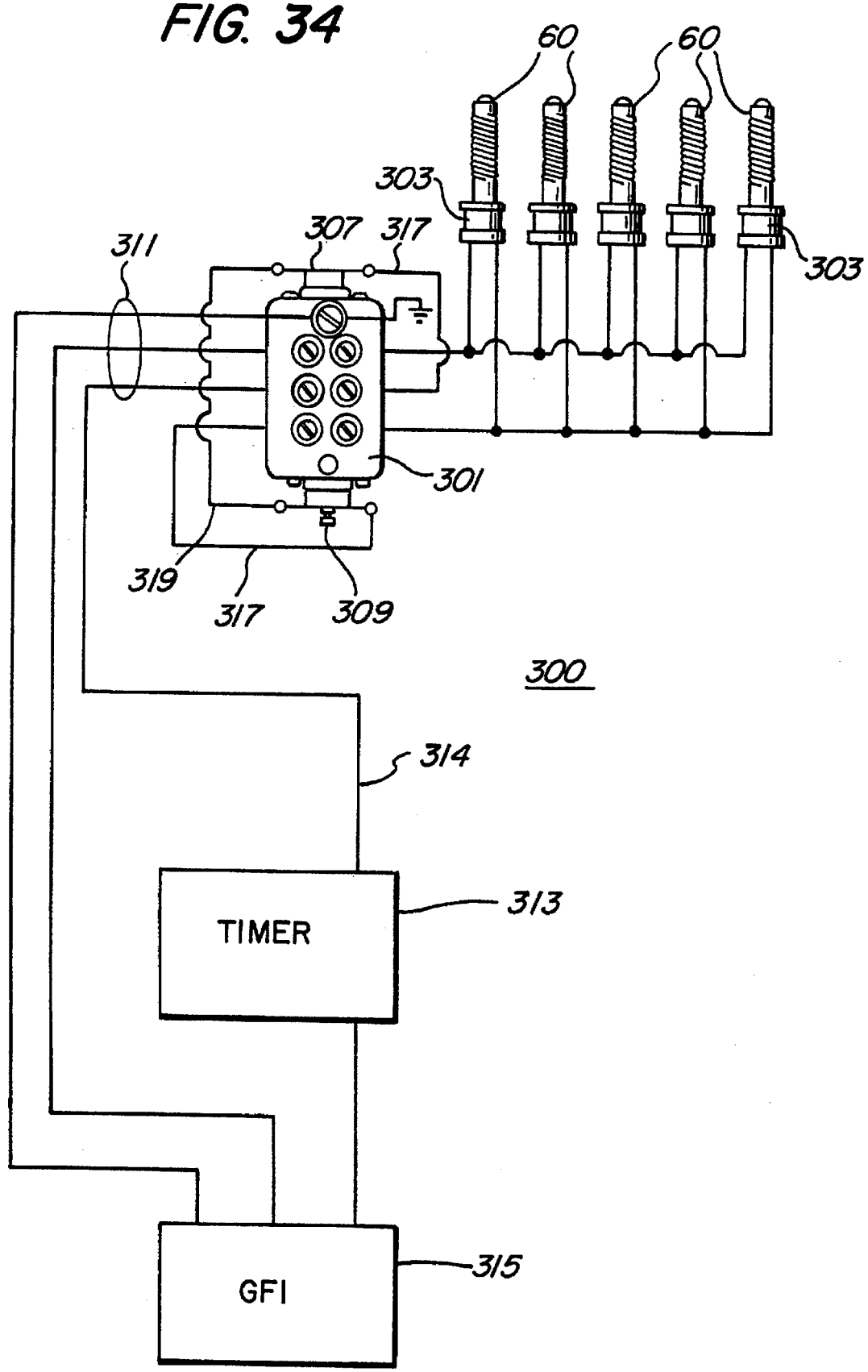
FIG. 34 an electrical schematic diagram of electrical componentry of the preferred embodiment.

With respect to electrical componentry 300, as shown in FIG. 34, a suitable terminal block 301 may be provided with leads extending from the infrared heating elements 60, which may comprise igniters F 0206RC038 as available from Carborundum Company Igniter Division, Niagara Falls, N.Y. These elements 60 are thus placed in a domical recess in the ceiling of the sauna 11, the location most distant from users, where they provide illumination, as well as heating function. Additionally, the heater array is covered by the taut, knitted stainless steel mesh 59 to prevent accidental or purposeful user contact with the heating elements 60. The innermost domical element 58 may optionally be gold-plated on its reflective surface to enhance performance.

The silicon carbide heater elements 60 may be terminated in insulating porcelain bushings 303 that are installed in a grounded igniter retainer 305 (FIG. 4). The wires from the heater elements 60 to the terminal block 301 are preferably covered with two layers of high temperature insulation and terminated in a terminal block that also contains an automatic resetting overtemperature switch 307 which opens at 221°F. and an easily accessible manually resettable temperature switch 309 that opens at 250°F. The cord 311 from the terminal block to the mechanical timer 313 is rated for 105° C., 600VAC outdoor operation.

One embodiment has employed a 0 to 30-minute mechanical timer enclosed in a three-inch-diameter clear, acrylic spherical shell or container with no exposed or accessible metal components. Other embodiments may include electronic timers and injection molded housings. The cord from the control to the input plug is rated for 90°C, 600 VAC outdoor operation and terminated in a two-conductor ground fault circuit interrupter 315. The timer container may also house lights to indicate operation or to provide interior illumination to users when the heaters are not in operation. All electrical components are preferably U.L. listed.

To operate such a sauna 11, the user sets the 0 to 30-minute rotary mechanical timer or electronic timer which provides power to the silicon carbide resistive heating elements 60 in the domical element located in the ceiling. The heating elements 60 reach operating temperature within 30 seconds due to their low thermal mass, bathing users with warm radiant heat directly and via reflections from the metallized inner skin, which is an effective reflector of radiant heat. This method of operation means the walls and the contained air do not have to be heated to provide an effective thermal environment and allows for fast warm-up in addition to providing low energy usage. Thus, although the air in the sauna 11 is heated during use, this is not the primary heating method.

Saunas constructed according to the preferred embodiment may be six feet high, five feet in base diameter, and can be installed indoors on any kind of conventional flooring or outdoors on smooth level surfaces such as concrete, asphalt, stone, brick, wood decks, or patios. Rubber bumpers are provided to raise the sauna approximately ⅛-inch above the floor/ground surface by attachment to the bottom of the sauna foot 43. The user's environment may be further enhanced by air purifiers, air ionizers, odorants, seat cushions, and a central element which spans the seats and effectively brings the floor up to seat height.

Saunas installed outdoors must be fastened to the supporting surface or to a heavy base to prevent damage or overturning due to winds. It has been calculated that the preferred embodiment can withstand 30-mph winds without tipover (unoccupied).

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed:

1. A sauna comprising:
   a space frame comprised of a plurality of arched tube members joined at the top to a dome comprising a plurality of domical elements;
   a flexible skin installed over said tube members;
   a seat means for seating occupants located within said skin and attached to said space frame;
   a floor removably attached to said skin; and
   infrared heating means attached to one of said domical elements for heating said sauna.

2. The sauna of claim 1 wherein said dome is detachable from said space frame, said skin is removably installable about said space frame, and said seat means is removably detachable from said space frame, thereby lending portability to said sauna.

3. The sauna of claim 1 wherein said skin comprises a plurality of sections zippered together.

4. The sauna of claim 1 further including toweling means removably installable in said sauna for covering said seat means.

5. The sauna of claim 4 wherein said floor means comprises a floor structure laced to the lower edge of said skin.

6. The sauna of claim 4 wherein said floor means comprises a floor comprising respective vinyl sheets attached by fastening means to said skin.

7. A sauna comprising:
   an enclosure having a top, a bottom, and a door therein, said enclosure comprising:
      a space frame structure comprising a plurality of arched tubes, and
      a skin wrapped about said tubes to form said enclosure, said skin comprising a plurality of sections, each having an outer fabric fastened to an inner fabric, said inner fabric including an elastic portion therein;
   means positioned at the top of said enclosure for mounting an infrared heater in the top of said enclosure; and
   an infrared heater mounted by said means for mounting.

8. A sauna comprising:
   an enclosure having a top, a bottom, and a door therein;
   means positioned at the top of said enclosure for mounting an infrared heater in the top of said enclosure, said means comprising a plurality of domical elements, and means for mounting said domical elements one above the next; and
   an infrared heater mounted by said means for mounting.

9. The sauna of claim 8 further including means for spacing each of said domical elements apart from one another so as to control the temperature of each of said domical elements.

10. A sauna comprising:
    an enclosure having a top, a bottom, and a door therein, said enclosure comprising:
       a space frame structure comprising a plurality of arched tubes, and
       a skin wrapped about said tubes to form said enclosure;
    means positioned at the top of said enclosure for mounting an infrared heater in the top of said enclosure;
    an infrared heater mounted by said means for mounting; and
    a plurality of feet, one mounted to the lower end of each of said arched tubes, and a plurality of base members attached to said feet.

11. A sauna comprising:
    an enclosure having a top, a bottom, and a door therein, said enclosure comprising:
       a space frame structure comprising a plurality of arched tubes, and
       a skin wrapped about said tubes to form said enclosure;
    means positioned at the top of said enclosure for mounting an infrared heater in the top of said enclosure;
    an infrared heater mounted by said means for mounting;
    a door frame means for providing an opening in said skin;
    means for hingedly mounting said door to said door frame means; and
    means for latching said door to said door frame means, said means for latching comprising a magnetic latch comprising:
       at least one disc-shaped metallic door strike attached to said door frame means, and
       at least one disc magnet attached to said door.

12. The sauna of claim 11 further including a first door handle mounted to the inside of said door.

13. The sauna of claim 12 further including a second door handle mounted to the outside of said door.

14. The sauna of claim 13 wherein said second door handle is mounted to said door by a mounting means comprising:
    a handle plate having a body portion comprising a left half and a right half, and first, second, third, and fourth winged regions extending from said body portion.

15. The sauna of claim 14 further including toweling means for covering the seats of said sauna.

16. The sauna of claim 15 further including floor means for providing a floor within said sauna.

17. The sauna of claim 16 wherein said floor means comprises a floor structure laced to the lower edge of said skin.

18. The sauna of claim 16 wherein said floor means comprises a floor comprising respective vinyl sheets attached by fastening means to said skin.

* * * * *